United States Patent
Chauhan et al.

(10) Patent No.: US 7,494,466 B2
(45) Date of Patent: Feb. 24, 2009

(54) ULTRASONIC TREATMENT OF BREAST CANCER

(75) Inventors: Sunita Chauhan, Singapore (SG); Wan Sing Ng, Singapore (SG)

(73) Assignee: Nanyang Technological University, Singapore (SG)

( * ) Notice: Subject to any disclaimer, the term of this patent is extended or adjusted under 35 U.S.C. 154(b) by 272 days.

(21) Appl. No.: 10/501,819

(22) PCT Filed: Jan. 21, 2003

(86) PCT No.: PCT/SG03/00014

§ 371 (c)(1),
(2), (4) Date: Oct. 27, 2004

(87) PCT Pub. No.: WO03/059434

PCT Pub. Date: Jul. 24, 2003

(65) Prior Publication Data

US 2005/0038339 A1 Feb. 17, 2005

(30) Foreign Application Priority Data

Jan. 21, 2002 (SG) .............................. 200200342-4

(51) Int. Cl.
*A61B 8/00* (2006.01)
*A61H 1/00* (2006.01)
(52) U.S. Cl. .......................................... 600/439; 601/2
(58) Field of Classification Search ................. 600/411, 600/439, 459, 564; 601/2; 606/167; 310/322, 310/334

See application file for complete search history.

(56) References Cited

U.S. PATENT DOCUMENTS

| | | | | |
|---|---|---|---|---|
| 4,836,191 | A | * | 6/1989 | Noske et al. .................... 601/4 |
| 5,501,655 | A | * | 3/1996 | Rolt et al. ........................ 601/3 |
| 5,522,869 | A | | 6/1996 | Burdette |
| 5,549,638 | A | | 8/1996 | Burdette et al. |
| 6,778,848 | B1 | | 8/2004 | Bechtold et al. |

FOREIGN PATENT DOCUMENTS

DE 19745400 C1 4/1999

* cited by examiner

*Primary Examiner*—Eric F Winakur
*Assistant Examiner*—Michael T Rozanski
(74) *Attorney, Agent, or Firm*—Dinsmore & Shohl LLP (57) ABSTRACT

A method of treatment, clinical treatment assembly, robotic manipulator and controlling arrangements for the treatment of cancers are described. The invention has particular application in the treatment of breast cancer. A robotic manipulator (18) carries a jig assembly (30). The jig assembly (30) includes an array of treatment probes (52, 54, 56) and a single identification/diagnostic probe (58). The probes can be moved by the robotic manipulator (18) in three directions (x, y, θ). A subject breast tissue is received in a tank (16) through an operating window (14), and the robotic manipulator (18) is to firstly determine the site of a tumor in the breast tissue. Once the tumor has been located by use of the identification/diagnostic probe (58), the treatment probes (52, 54, 56) are used to ablate the tumor by the superposition of ultrasonic waves at a focal region. A series of such lesions may be performed in sequence to traverse the full extent of the tumor.

29 Claims, 9 Drawing Sheets

ULTRASONIC TREATMENT OF BREAST CANCER

FIELD OF THE INVENTION

This invention relates to the treatment of cancers. It relates particularly to the use of focused ultrasonic energy to treat cancers/tumours in the breast, and in the organs through the clear acoustic window of the abdominal and supra-pubic routes.

BACKGROUND OF THE INVENTION

Cancer is a life-threatening medical condition that is deserving of serious scientific and medical investigation with a view to finding improved curative treatments. Breast cancer is the most frequent form that occurs in women. Other common susceptible sites in the abdomen—affecting both men and women—are the kidney, liver, colon and stomach.

Two broad categories of cancer treatment are: direct surgical manipulation on the affected tissue and non-invasive treatment. Non-invasive techniques utilise modalities such as X-rays, lasers, microwave, hyperthermia, cryoablation etc., the selection of which depends upon the stage, size, shape and position of the target area. Ultrasound is known to be useful as one form of hyperthermia. Single focused transducers, however, are not very flexible in creating a desired spatial distribution of ultrasound energy within the treatment field. This is because they have a fixed focal depth and frequency of operation. Also, the size of the focal region may not match the size of the tumour. To treat the whole abnormal region, an ultrasonic beam needs to be mechanically scanned over the target area Besides this, the residual amount of energy residing in dispersion zone and its overlap during scanning over the target region may result in undesirable hot-spots in the overlying normal tissue.

High Intensity Focused Ultrasound is a non-invasive technique capable of selective destruction of tissue volumes within the body. The aim is to produce damage in the focal region of an acoustic beam in a predictable and reproducible manner, while sparing overlying and surrounding tissue. A specific multi-probe technique, such that the individual probes are excited in unison, at comparatively low power levels, is known.

One example of this known approach—for use in the treatment of brain cancers—is described in the publication: Chauhan, S, Davies, B. L., Lowe, M. J., 'A Multiple Focused Probe System for HIFU-based Neurosurgery', *Ultrasonics*, vol 39, 33-44, 2001. This approach, as outlined in the publication, is not directly applicable to the treatment of abdominal and breast cancers. There are important anatomical differences between the human torso and head, most notably the bone enveloping the brain. As such, no immediate acoustic window to the brain is available without removing a section of the skull. This limits the ability to manipulate the orientation of the ultrasonic transducers. In the abdomen, it is the ribs that pose obstacles to an acoustic window, however there are interstices between the ribs that make orientation of the ultrasonic probes easier.

It is an object of the present invention to provide a form of focused ultrasonic treatment of cancers that seeks to improve the efficacy of such a modality, and reduce the unwanted damage to normal tissue.

SUMMARY OF THE INVENTION

The invention discloses a method for the ultrasonic treatment of a cancer in subject tissue, comprising the step of: robotically manipulating an array of two or more ultrasonic treatment probes, that are mechanically focused onto a con-focal region, to sight said focal region on at least a portion of a target tumour whose site is determined by ultrasound.

The above step may be preceded by the step of determining the site of a target tumour by ultrasound. The above step may be succeeded by the step of activating said probes to ablate said portion of the target tumour The invention further discloses apparatus for the ultrasonic treatment of cancer in subject tissue, comprising:

an array of (i) two or more ultrasonic treatment probes, that are mechanically configurable to be focused onto a desired con-focal region, and (ii) an ultrasonic identification probe;

a robotic manipulator, carrying said array, and operable to move said array and thus sight said focal region; and a programmed controller which operates to activate said probes and said cause motion of robotic manipulator in a manner such that the identification probe is scanned over at least a portion of the tissue to determine the site of a target tumour, and the treatment probes are sighted such that the focal region coincides with at least a portion of the target tumour and are activated to ablate said portion of the target tumour.

The invention yet further discloses a jig array assembly for ultrasonic treatment probes comprising:

a central shaft;

two or more segmented collars, in a stacked manner rotatably of said shaft, and adapted to be fixed in a chosen orientation by fastening means;

a respective mounting member extending from each said collar, and providing mounting point, said mounting point lying in a common plane orthogonal to said shaft;

a respective arm attached at the end to a respective mounting point; and a respective probe holder attached to the other end of each said arm.

BRIEF DESCRIPTION OF THE DRAWINGS

The invention is further described by way of non-limitative example, with reference to the accompanying drawings, in which.

DETAILED DESCRIPTION

An embodiment will be described with reference to the treatment of breast cancer. In particular, a method of treatment, a clinical treatment assembly, a robotic manipulator and controlling arrangements therefor will be described. It should be understood, however, that the invention is not so limited. The various aspects are equally applicable to the treatment of other forms of cancer through soft tissue acoustic windows. Embodiments of the invention also can be applicable in a purely diagnostic mode.

In summary, a method of treatment, clinical treatment assembly, robotic manipulator and controlling arrangements for the treatment of cancers are described. The invention has particular application in the treatment of breast cancer. A robotic manipulator carries a jig assembly. The jig assembly includes an array of treatment probes and a single identification/diagnostic probe. The probes can to be moved by the robotic manipulator in three directions. A subject breast tissue is received in a tank through an operating window, and the robotic manipulator is firstly to determine the site of a tumour in the breast tissue. Once the tumour has been located by use of the identification/diagnostic probe, the treatment probes are used to ablate the tumour by the superposition of ultrasonic waves at a focal region. A series of such lesions may be performed in sequence to traverse the full extent of the tumour.

Mechanical and Electrical Arrangement

Figure 1:
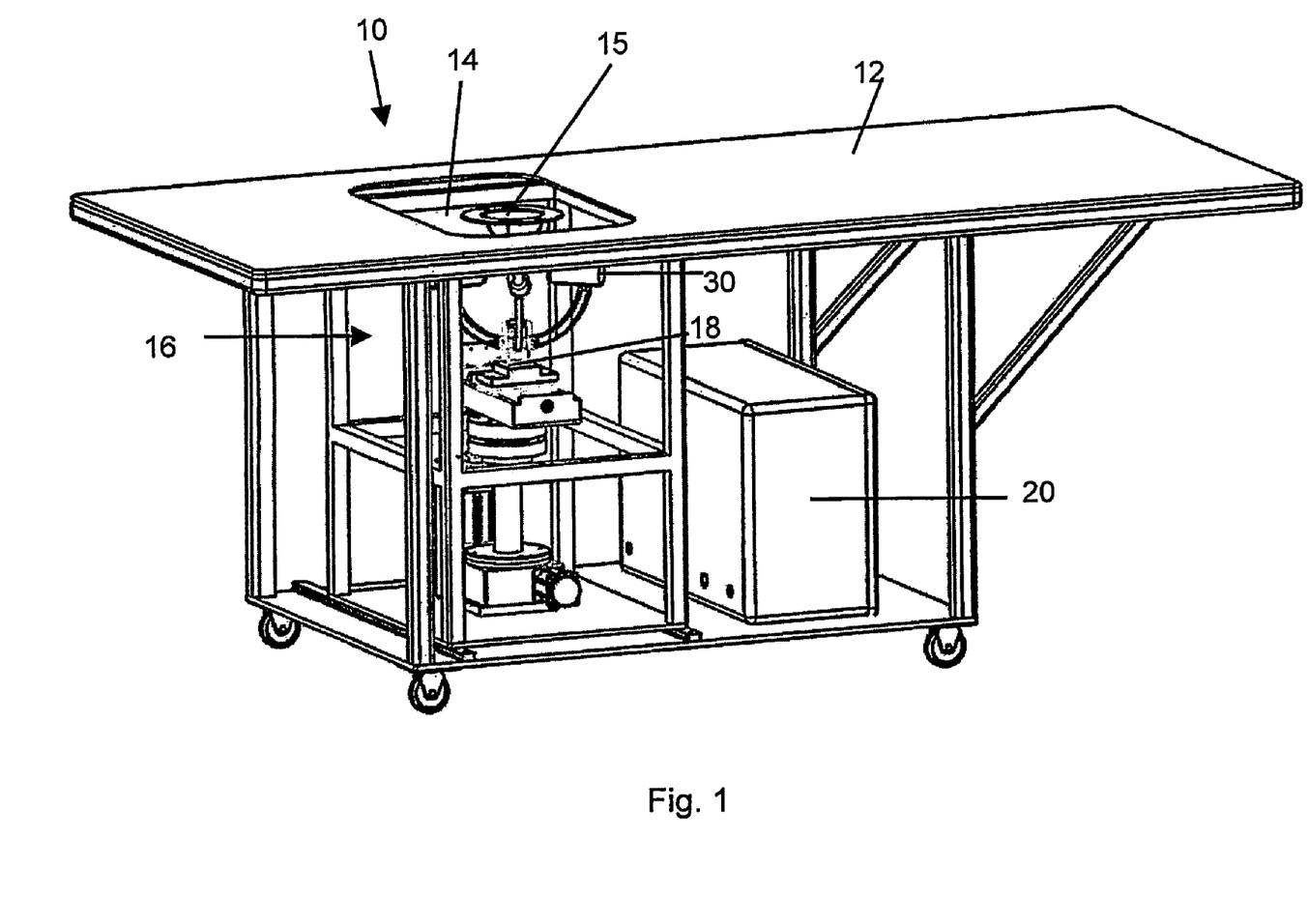
FIG. 1 is a perspective view of a surgical treatment assembly.

FIG. 1 shows a surgical treatment assembly 10 in broad detail. An operating table 12 has an operating window 14 that is arranged to receive the patient's breasts. The subject breast is received into a half-hemispherical framed cup 15 to descend into a tank 16 containing a coupling medium (e.g. degassed water). The patient's breasts are isolated from the couplant by an elastic membrane forming a boundary of the operating window 14. Suitable forms of membrane include latex or polyurethane. A robotic manipulator 18 is sited partially underneath and partially within the tank 16, and carries the ultrasonic probe assembly 30 used for the treatment of the subject breast Operational controls are housed within a cabinet 20, mounted on the base of the operating table 12. The relative location of the frame 15 and the robotic manipulator 18 is such that the subject breast will be within the range of motion of the robotic manipulator.

Figure 2A:
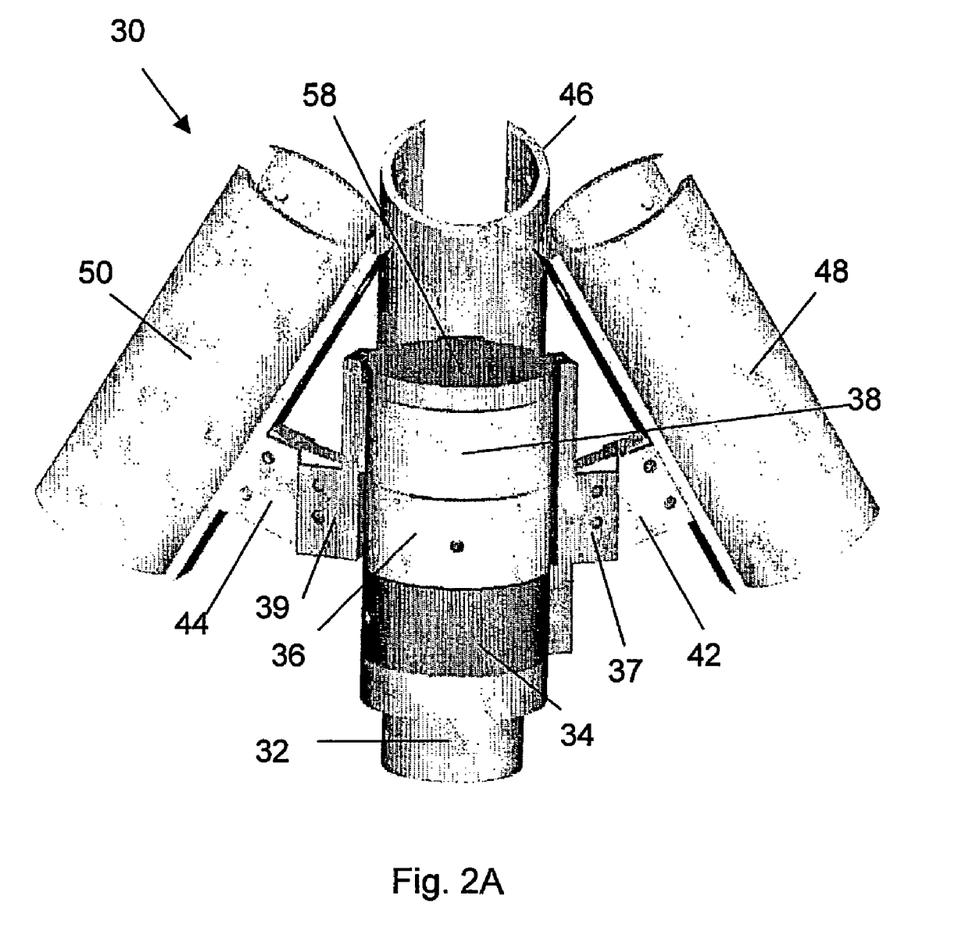
FIGS. 2A, 2B and 3 are perspective views of a probe jig assembly in three configurations.

Turning then to FIG. 2A, a first form of jig assembly 30 is shown. A central shaft 32 has three segmented collars 34, 36, 38 arranged in a stacked manner on the shaft. Each collar can rotate about, and be fixed into position on the shaft, typically by a grub screw or the like (not shown). Each collar has attached to it a mounting member 35, 37, 39. The top and bottom mounting members 35, 39 in the stack provide an offset such that all three members provide a mounting point that is co-located in the horizontal plane through the central collar 36 (i.e. having a common origin). Extending from the mounting point of each mounting member 35, 37, 39 is an arm 40, 42, 44, at the free end of which is a sleeve 46, 48, 50, into which is received respective ultrasound transducer probes. These probes 52, 54, 56 are best seen in FIG. 2B.

The orientation of the probes can be adjusted to give a desired con-focal region by the relative positioning of the arms 40, 42, 44 with respect to the shaft 32 (i.e. the inter-probe angle), and the respective lengths of the arms 40, 42, 44. These relative lengths determine the angles of the sleeve 46, 48, 50 (and thus the respective probes 52, 54, 56) from the horizontal plane. The embodiment of FIG. 2A differs from that of FIG. 2B in this regard.

Figure 2B:
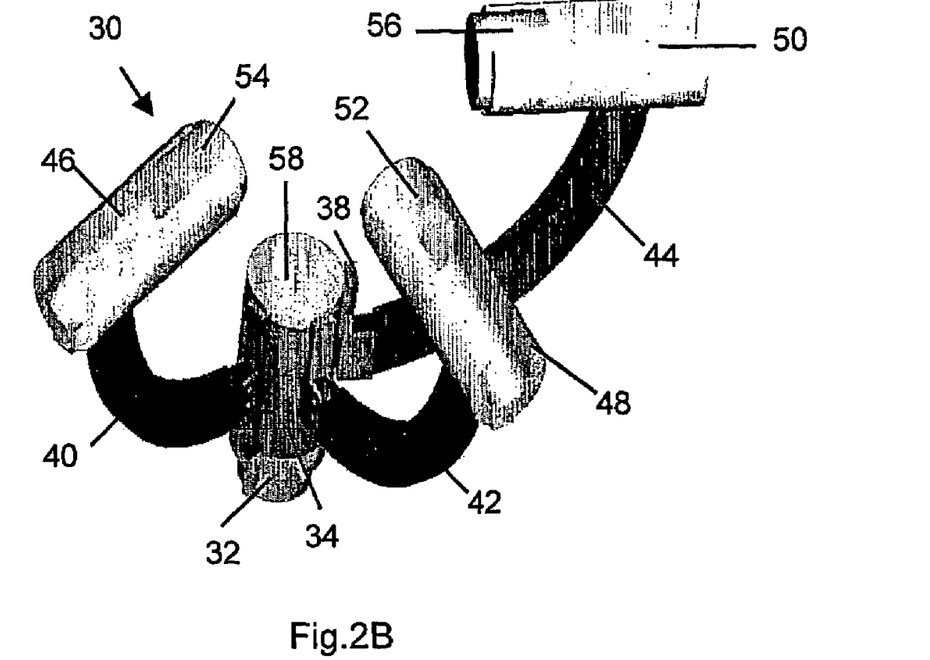
Figure 3:
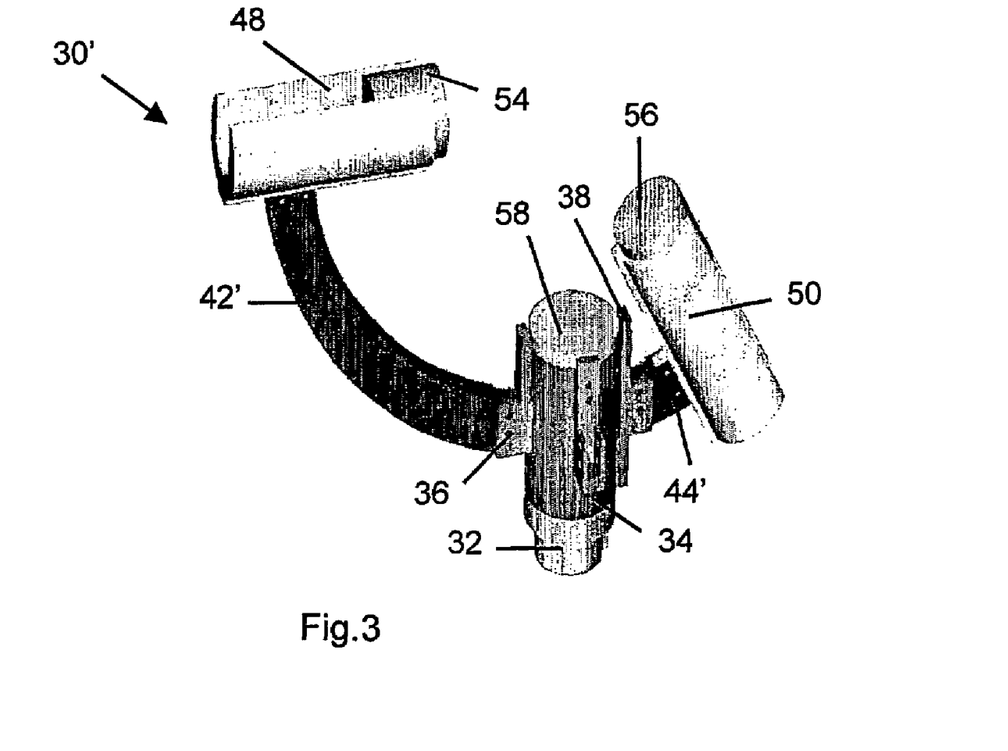

For the configuration of FIGS. 2A and 2B, a symmetrical focal region is achieved. For the example of FIG. 3, in which only two probes are in use, a focal region of an irregular (thin) shape is achieved. The range of adjustments described allows a focus region to be identified within a half-hemispherical volume of space; this broadly representing the volume occupied by a breast.

The resultant shape of focal region can be manipulated further by the choice of probe, such that small clusters of cancer cells can be sighted. It is envisaged that the minimum number of treatment probes is two, since a degree of superimposition must be achieved in the focus region. Equally, more than three probes may be utilised—the decision is a clinical one based upon the location and localised shape of the subject tumour itself. In other words, a desired spatial focal region is designed by way of the number, type and relative orientation of the probes.

The treatment probes typically are extra-corporeal, spherical bowl types, operating in unison at 2 MHz and a focal depth of 65-80 mm. The focal region of an individual probe is oblate in shape with typical dimensions of 18 mm and 1.5 mm. In the multiple probe approach, the desired flexibility can be achieved in the shape, size and energy distribution within the con-focal region by orienting the probes in a specific configuration.

The ultrasonic radiation from the respective probes 52, 54, 56 superimposes in a con-focal manner so that there is, in combination, a heating effect sufficient to raise the temperature in that focal region to ablate the targeted cancer cells. The surrounding tissue, through which the respective ultrasonic waves pass, is spared.

Of course, once the probes are fixed into alignment it is only movement of the shaft 32 that can 'move' the focal region in space. In other words, a cancer in the breast typically is of a far greater size then the focal region, and thus a path needs to be traversed by the focal region in order to ablate the entire tumour site. This function is achieved by the robotic manipulator 18.

The shaft 32 is adapted to receive at its free end a further ultrasonic identification/diagnostic probe 58. The purpose of this probe 58 is to provide an image of the target tissue as a function of distance, that can be used to define positioning of the focus region achieved by the treatment probes, as will be explained in further detail below.

Figure 4:
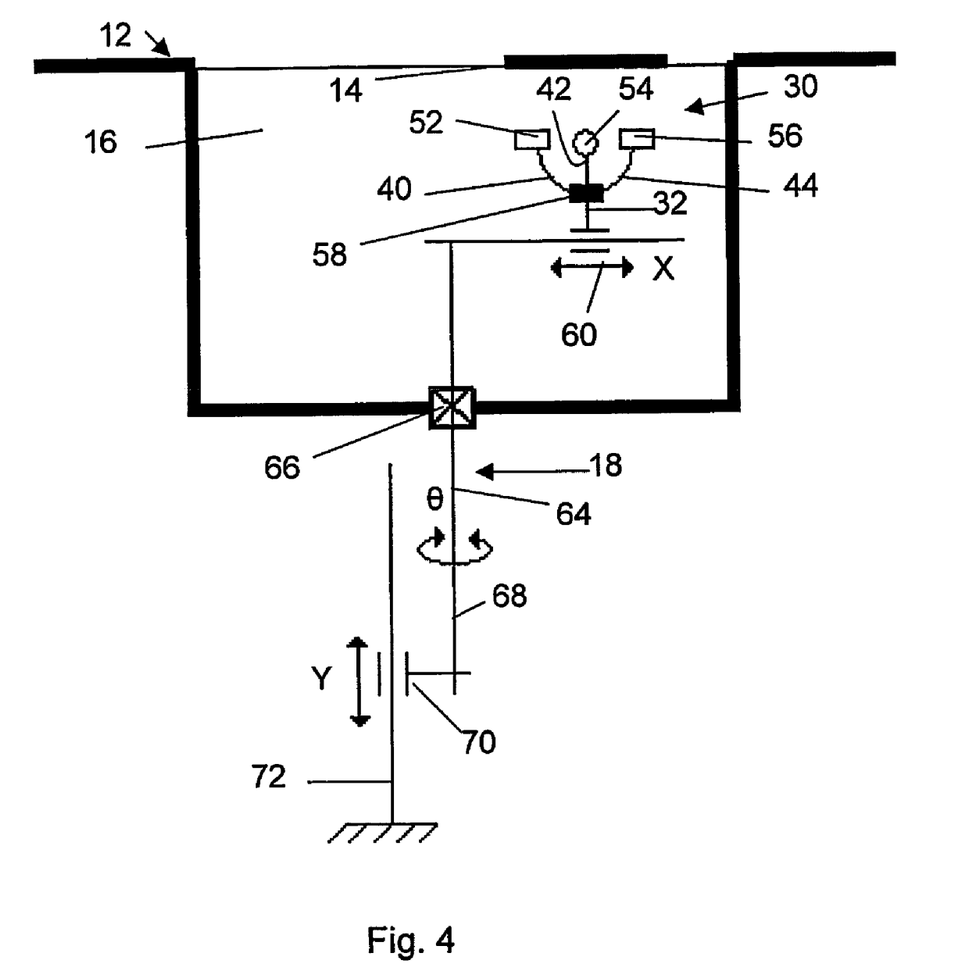
FIG. 4 is a schematic diagram showing the range of controlled movement that may achieved by the robotic manipulator.
Figure 5:
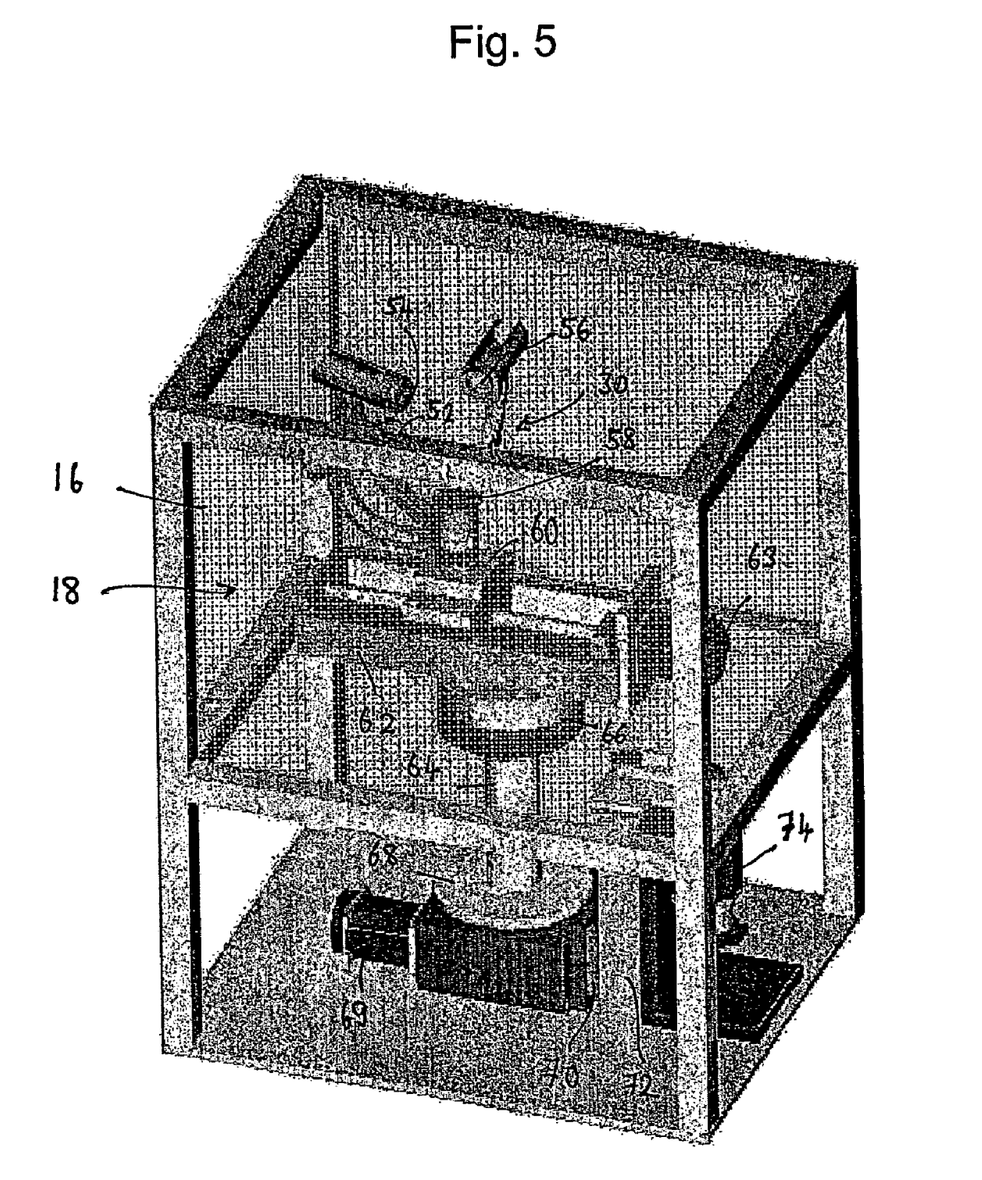
FIG. 5 is a perspective view of the robotic manipulator assembly.

Referring then to FIGS. 4 and 5, these show, respectively, a generalised schematic diagram and a detailed mechanical arrangement drawing of the location of the robotic manipulator 18 and the jig assembly 30 within the tank 16. The shaft 32 supporting the three probes 52, 54, 56 mounts from a carriage 60 that is able to be moved, in a controllable manner, in the horizontal plane carried on a platform 62, by an electrical motor 63. The platform 62 is mounted on a further shaft 64 that passes through a water-tight joint 66 in the base of the tank 16, terminating on a rotary stage 68. The stage causes the shaft 64 to be rotated by a further electrical motor 69. The rotary stage 68 is carried by a further carriage 70 that mounts from a vertical platform member 72. A yet further electrical motor 74 causes the carriage 70 to be controllably moveable in the vertical plane. The x and y motion can be achieved by a screw thread or belt-driven arrangement. Other arrangements, apparent to one skilled in the art, also are possible. In this way a 3-axis (x, y, θ) robotic manipulator is achieved.

Plainly, the elements of the robotic manipulator within the tank need to be appropriately protected from water ingress.

Figure 6:
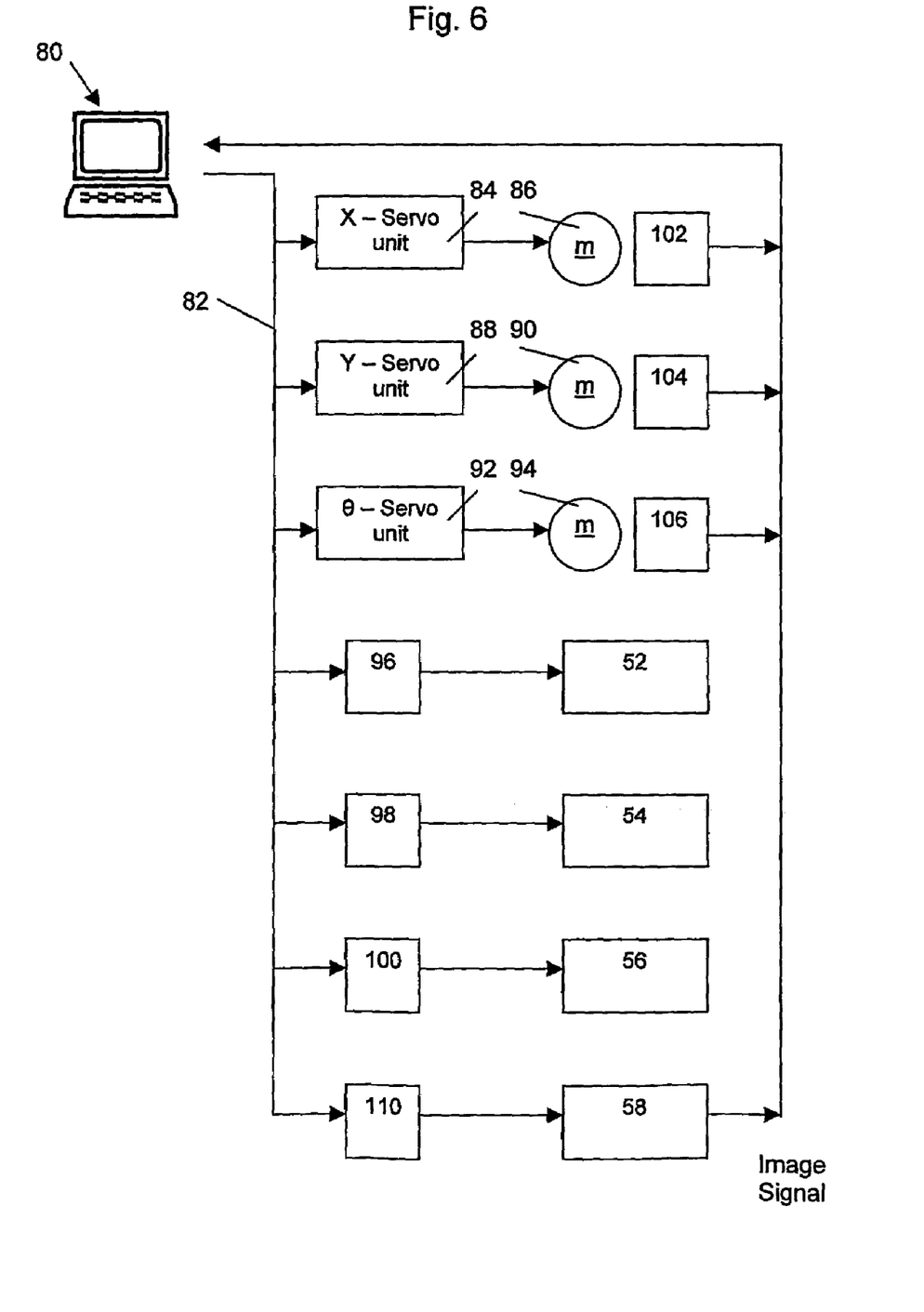
FIG. 6 is a schematic block diagram showing the control circuitry and interface to the robotic manipulator.

FIG. 6 shows an electrical schematic diagram representing control and signalling for the robotic manipulator, and the treatment and identification/diagnostic probes. A PC-based computer 80 is programmed to control the operation of the robotic manipulator and the probes in a manner that will be described below. It has an output control signal bus (of any inconvenient form) which provides control signals to three servo-controllers, respective being for the 3-axis movement of the robotic manipulator. The x-servo unit 84 drives the x-axis motor 86. The z-servo unit 88 drives the z-axis motor 90. The θ-servo unit 92 drives the θ-axis motor 94.

The control signals also control the respective amplifier units 96, 98, 100 that provide power to excite the respective treatment probes 52, 54, 56. Each of the motors 86, 90, 94 of the robotic manipulator includes a form of optical encoder 102, 104, 106 that provides a relative location (i.e. distance) feedback signal on the input data bus 108.

A diagnostic drive unit 110 provides excitation to the identification/diagnostic probe 58. The probe 58 returns an ultrasound image of a scanned field as a function of distance. This image signal is provided to the input data bus 108.

Identification (Diagnostics) and Treatment

Figure 7:
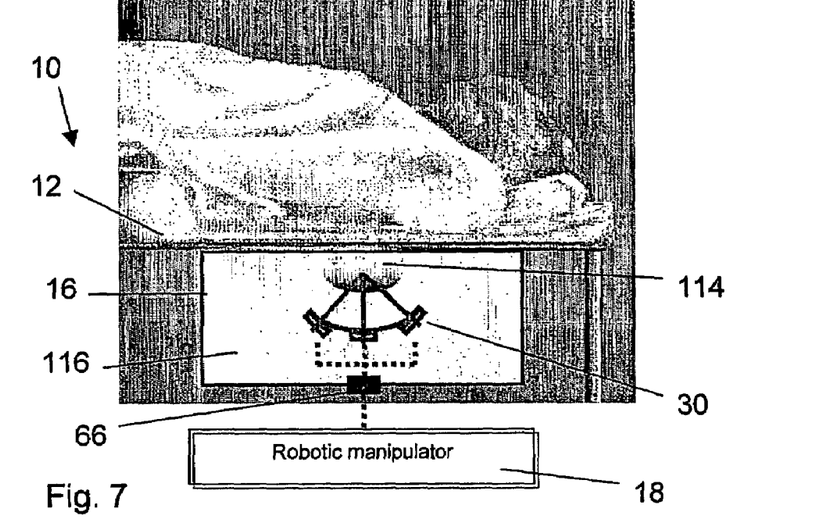
FIG. 7 shows the clinical treatment assembly in use.
Figure 8:
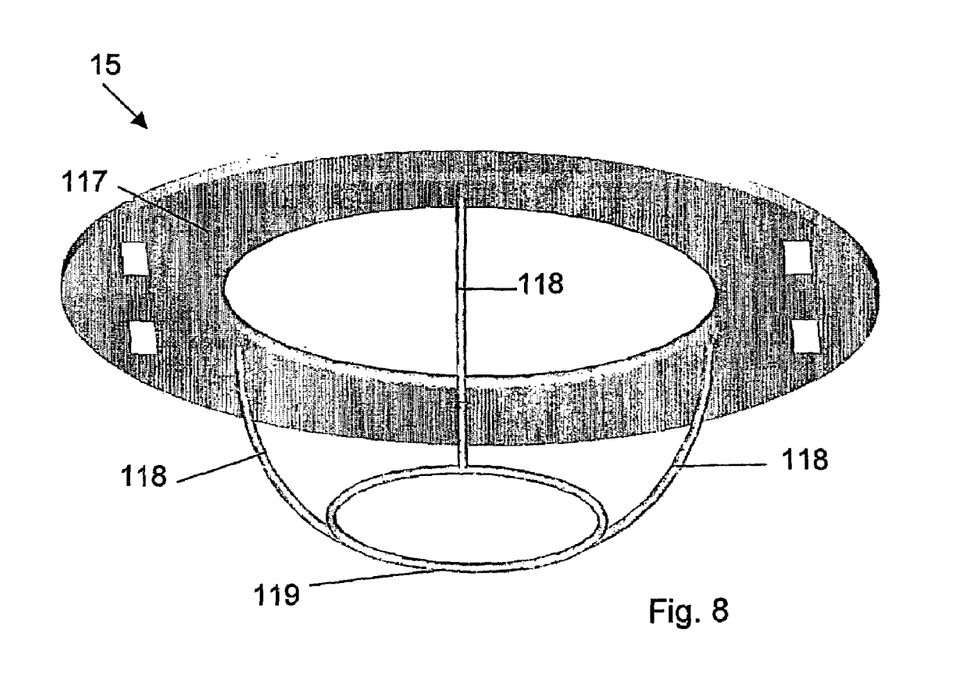
FIG. 8 is a perspective view of a framed cup element of the surgical treatment apparatus.

FIG. 7 shows the surgical assembly 10 in use. A subject lies face down (i.e. prone) on the operating table 12. The subject breast is received in the framed cup 15 to descend through the operating window 14 being supported by an elastic membrane 114. The framed cup 15 is shown in detail in FIG. 8, having a rim 117, and three arcuate arms 118 ending in a ring 119. The tank 16 is filled with degassed water 116, providing a medium/couplant for effective transfer of ultrasound energy into the breast. The jig assembly 30 has been mechanically pre-configured and is under control of the robotic manipulator 18. Diagnostics or identification and treatment is then undertaken.

Identification (Diagnostic) Mode

The identification (diagnostic) mode is used to determine the location of, and shape of cancerous tissue in the breast. This is achieved by use of the identification/diagnostic probe 58 which is arranged to propagate an ultrasonic wave to a known depth into the breast and then progress in the z-axis to perform a slice-wise scan of the breast. The breast is mapped to a coordinate system operating in three dimensions (typically a Cartesian system). Such a procedure can be useful to diagnose tumours in the breast, without subsequent implementation of the ultrasonic treatment, since it may be the cell cluster is a benign lump or cyst, or chosen to implement an alternative modality of treatment.

Planning and Treatment Mode

Figure 9:
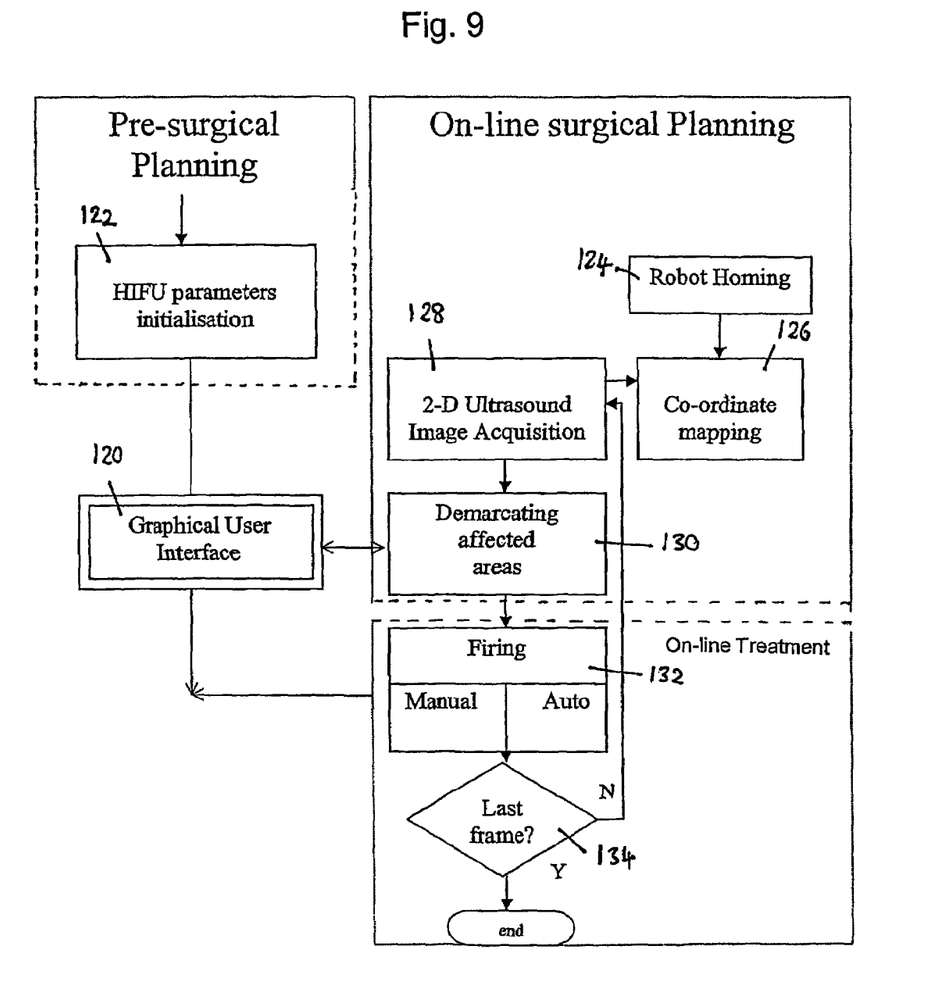
FIG. 9 is a schematic block diagram of the operational modes of the surgical treatment.

Referring now to FIG. 9, a block flow diagram shows the logic flow of pre-surgical planning and on-line surgical planning. Central to the pre-surgical and on-line surgical planning is the provision of a graphical user interface 120. In other words, the pre-surgical and on-line procedures are undertaken by the physician solely by use of the GUI 120.

The pre-surgical planning constitutes the initialisation of HIFU parameters that effect the thermal dose (step 122). These parameters include the electrical power levels to individual probes (calculated from the acoustical intensity required for ablation in a particular tissue/organ type, taking in to account the transducer probes' specifications), exposure time, probe orientation, and couplant temperature. The exposure parameters depend on the shape, size and extent of the cancer/tumour, as deduced by the radiologist/oncologist during pre-surgical analysis/diagnosis, and define the thermal dose. Indeed, the characteristic of the tumour can be determined from the identification (diagnostic) mode of operation of the apparatus (discussed above) or by other, conventional imaging modalities. The joint power levels typically are in the ranges: 100-150 W (electrical), which manifests itself into an acoustic intensity in the exposures (i.e. lesions) formed that are required to ablate the target tissue. The typical exposure levels are 2-8 sec with a subsequent cooling of 10-15 sec at a given exposure site.

In the on-line surgical planning, the subject, in an anaesthetised state, is firstly accommodated, as discussed with reference to FIG. 7, then an initial robot homing operation is performed (step 124) whereby the robotic manipulator defines its coordinates system (step 126). The identification/diagnostic probe 58 has a role here in proximity sensing or localisation with reference to the site.

It is now necessary to accurately relocate the tumour, i.e. notwithstanding that this has been performed in the pre-surgical planning stage (step 128). This is achieved through use of the identification/diagnostic probe 58, that is robotically manipulated to image a series of two-dimensional slice (typically saggital) through the breast. The physician is able now to confirm the pre-surgical planning (or make adjustments to the relevant parameters), but otherwise has confidence that the robotic manipulator has spatial accuracy with respect to the actual location of the subject tumour.

Figure 10:
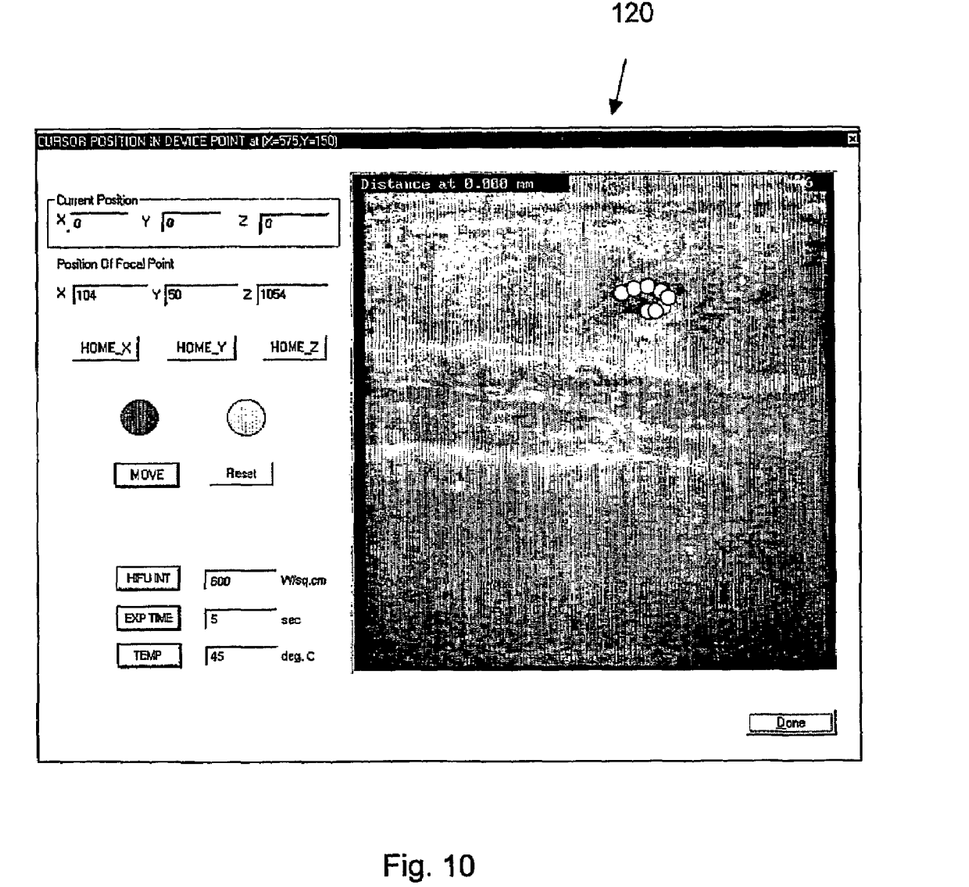
FIG. 10 shows a sample display representing surgical planning using a graphical user interface.

The physician now has a pseudo three-dimensional image of the breast from which the location of a tumour can be accurately determined. The physician now demarcates the affected area of the breast (step 130). References is made here to FIG. 10, which is a single frame (i.e. single slice) of the graphical user interface 120 showing the process of demarcation.

The physician has the choice of siting a single lesion, siting as series of lesions in a single plane, or siting lesions for the whole volume of the tumour before applying the focused ultrasonic treatment. One of the considerations in making this choice is that the shape of the tumour may change after treating any individual lesion.

Once the set of lesions has been so identified, then the surgical procedure may commence by application of treatment energy to the configured treatment probes, 52, 54, 56 (step 132). Such treatment can be in an automatic or manual mode. In other words, the robotic manipulator can be controlled by the physician to 'fire' and then site the next lesion, or the robotic manipulator can execute all lesions in a programmed manner. The treatment ends when the last frame is reached (step 134).

For the present apparatus, the concept of safety is grossly different from industrial robots, that aren't designed/configured to work in vicinity of human beings. Surgical/medical robots are required to function near and 'inside' humans, with human co-operation and intervention, thus safety principles cannot be adopted directly from fully autonomous and versatile industrial machines. Due to the precarious nature of human anatomy and physiology, and thus the suitably selected medical for a particular treatment, a surgical/medical robot must be the subject of a stringent safety regimen.

Mechanically, the robotic system is configured to move in a restricted and well-defined work-envelope. The practical work-envelope of the manipulator encompasses the human torso, and thus is capable to reach and treat cancers/tumours through soft tissue windows in this region (such as breast tissue, trans-abdominal, supra-pubic and rib interstices). However, for a specific intervention in a specific tissue (i.e. in a breast, as described above) and after patient registration and homing stage, the robot is configured to move the jig assembly 30 only in a subset of the available work-envelope with suitably demarcated 'go' and 'no-go' areas. Safety limit switches and mechanical interlocks may be provided to restrict the motion in that area only. The primary control, however, is to restrict the trajectory by software. For instance, in the case of breast tissue, an annular cylindrical area is allowed as 'go' area. The radius of the 'no-go' inner cylinder is same as the framed cup 15, followed by a 'go' outer annular ring area with extended radius equivalent to the focal depth of selected ultrasonic probes, followed by a 'no-go' area in rest of the tank. This is done to ensure the probes enveloping the descended breast can not hit the organ/tissue at any stage of intervention during the lesioning process.

Another safety feature can be incorporated in the energy deployment to the probes. The treatment typically comprises an exposure of 2-8 seconds, followed by cooling/dead time. The power supply to the robot is accordingly programmed such that the energy sub-system to the probes is dormant during any 'robot move' operation. Once the robot places the jig assembly 30 at a suitable lesioning position, the power to the robot is 'cut-off'. In this way, the robot can not more during the application of ultrasonic energy.

The embodiment described is with reference to treatment of breast cancer, however, as foreshadowed, treatment of other cancers through abdominal or trans-pubic routes are contemplated. The surgical assembly would need to be modified to provide the appropriate acoustic window onto the body and the jig assembly also may need to be reconfigured to better suit the gross physical anatomy of the treatment site.

Embodiments of the invention offers specific advantages in that there is precise control over the ultrasonic energy to effectively ablate the site of tumours. Precise lesions may be obtained to give effective destruction of only the tumour cells. A reduction in the duration of intervention, and precise control in terms of crude and fine adjustments is made possible. The ability to treat the entire volume of a tumour under automatic robotic control removes the requirement of the physician/radiologist to have the extensive experience of visualising the three-dimensional region and manually guide a probe to the next suitable location/plane. Traditional surgery on a 2 cm tumour may take up to 2 hours to perform. In contrast, treatment by the present apparatus may take a greatly reduced time, even of the order of only 20 minutes. For example, the physician can chose to program and place any two subsequent lesions far away from each other in the affected region and thus optimising a lower or absent 'cooling zone' after each exposure. The reduced time under anaesthetic is beneficial to the subject.

Numerous alterations and modifications, as would be apparent to one skilled in the art, can be made without departing from the broad inventive concept.

The invention claimed is:

1. A method for manipulating treatment probes during ultrasonic treatment of a cancer in subject tissue, comprising:
   supporting a plurality of ultrasonic treatment probes with a jig assembly that comprises
   a central shaft extending along an axis,
   a plurality of collars coaxially mounted about said axis on said central shaft, and each of said collars independently rotatable about said axis, and
   a plurality of adjustable supports each attached to one of said collars, wherein each one of said plurality of ultrasonic treatment probes is received by one of said supports, and said collars are positioned about said axis and said adjustable supports are adjusted, to focus said plurality of ultrasonic treatment probes onto a con-focal region of a target tumour of said subject tissue; and
   robotically manipulating said plurality of ultrasonic treatment probes, by moving said central shaft, to focus said treatment probes onto said con-focal region on at least a portion of said target tumour whose site is determined by an ultrasound identification probe.

2. A method as claimed in claim 1, further comprising manipulating said plurality of ultrasonic treatment probes to sight on one or more other focal regions of the target tumour.

3. A method claimed in claim 2, wherein said manipulations are performed as a series of step-wise motions in one plane.

4. A method as claimed in claim 1, further comprising supporting said identification probe at the end of said central shaft and determining the site of the target tumour by ultrasound using said identification probe, prior to said robotically manipulating said plurality of ultrasonic treatment probes.

5. A method in claim 4, wherein said determining the site of the target tumour includes:
   ultrasonically scanning at least a portion of subject tissue in a series of step-wise slices by moving said jig assembly to derive a pseudo three-dimensional representation thereof.

6. A method as claimed in claim 1, further comprising preceding said robotically manipulating said plurality of ultrasonic treatment probes by mechanically configuring said plurality of ultrasonic treatment probes to give a desired convergent con-focal region.

7. A method as claimed in claim 1, further comprising, following said robotically manipulating said plurality of ultrasonic treatment probes, activating said plurality of ultrasonic treatment probes to ablate said portion of the target tumour.

8. A method as claimed in claim 7, wherein at least one of frequency, power and on-time of said plurality of ultrasonic treatment probes is adjusted.

9. A method as claimed in claim 7, further comprising, defining a safe working envelope for said robotic manipulation.

10. A method as claimed in claim 9, wherein said robotic manipulation is interlocked with said activation such that said robotic manipulation and said activation cannot occur simultaneously.

11. A method as claimed in claim 1, further comprising locating and orientating said plurality of ultrasonic treatment probes and a patient relative to each other, such that the target tumour site is within the range of motion of said plurality of ultrasonic treatment probes.

12. The method of claim 1, further comprising adjusting the length of each of said supports to focus said ultrasonic treatment probes onto said con-focal region.

13. The method of claim 1, further comprising supporting an identification probe at the end of said shaft to determine said site of said target tumour by ultrasound.

14. The method of claim 1, wherein at least three collars, three adjustable supports, and three ultrasonic probes are supported by said jig assembly.

15. The method of claim 1, wherein said manipulating further comprises mechanically moving said jig assembly linearly along said axis, while said ultrasonic probes remain stationary on said jig assembly.

16. The method of claim 1, further comprising positioning said jig assembly in three dimensions while said ultrasonic probes remain stationary on said jig assembly, to position said ultrasonic probes to sight said con-focal region on said at least a portion of said target tumour whose site is determined by ultrasound.

17. The method of claim 1, wherein said subject tissue is within a human breast.

18. Apparatus for the ultrasonic treatment of cancer in subject tissue, comprising:
   an away of (i) two or more ultrasonic treatment probes, that are mechanically configurable to be focused onto a desired con-focal region, and (ii) an ultrasonic identification probe;

a robotic manipulator, carrying said array, and operable to move said array and thus sight said con-focal region, wherein said ultrasonic treatment probes are supported by a jig assembly that comprises a central shaft extending along an axis, a plurality of collars coaxially mounted about said axis on said central shaft, with each of said collars independently rotatable about said axis, and a plurality of adjustable supports each attached to one of said collars, wherein each one of said ultrasonic treatment probes is received by one of said supports, and said collars are positioned about said axis and said supports are adjustable to focus said ultrasonic treatment probes onto said con-focal region; and a programmed controller which operates to activate said probes and cause motion of said robotic manipulator in a manner such that said ultrasonic identification probe is scanned over at least a portion of the tissue to determine a site of a target tumour, and said treatment probes are sighted such that said con-focal region coincides with at least a portion of the target tumour and are activated to ablate the portion of the target tumour.

19. The apparatus of claim 18, wherein said controller activates said robotic manipulator to sight and operate said treatment probes at other focal regions coinciding with the target tumour.

20. Apparatus as claimed in claim 19, wherein said controller activates said robotic manipulator as a series of step-wise motions in one plane to sight and operate said treatment probes in aggregation to coincide with the target tumour in that plane.

21. Apparatus as claimed in any one of claims 18, wherein said robotic manipulator operates to cause said identification probe to scan at least a portion of the subject tissue as a series of step-wise slices to derive a pseudo three-dimensional representation thereof.

22. Apparatus as claimed in claim 18, wherein said array of probes is mechanically configured to give a desired focal region matching to said site of the target tumour.

23. Apparatus as claimed in claim 22, wherein said ultrasonic treatment probes have predetermined parameters to be applied to the target tumour.

24. Apparatus as claimed in claim 18, further comprising a procedure table upon which a subject can lie, having an acoustic window therein at which the subject tissue is sited.

25. Apparatus as claimed in claim 24, wherein said acoustic window is arranged to be aligned with the breast of the subject.

26. Apparatus as claimed in claim 18, wherein said controller is programmed to define a safe working envelope for manipulation.

27. Apparatus as claimed in claim 26, wherein said controller further interlocks said treatment probes and said robotic manipulator so that both cannot be operated simultaneously.

28. A method for manipulating treatment probes during ultrasonic treatment of a cancer in subject tissue, comprising:

supporting a plurality of ultrasonic treatment probes with a jig assembly that comprises a support member defining an axis, a plurality of collars coaxially mounted about said axis on said support member and each of said plurality of collars is rotatable about said axis, and at least one arced arm attached to each of said plurality of collars, each said at least one arced arm supporting at least one of said plurality of ultrasonic treatment probes, wherein said plurality of ultrasonic treatment probes are received by said at least one arced arm to be focused onto a con-focal region of a target tumour of said subject tissue, said con-focal region remaining intersected by said axis as said plurality of collars is rotated about said axis; and robotically manipulating said plurality of ultrasonic treatment probes, to focus said treatment probes onto said con-focal region on at least a portion of said target tumour whose site is determined by an ultrasound identification probe.

29. An apparatus for treating cancer in a subject tissue, comprising:

an ultrasonic identification probe and a plurality of ultrasonic treatment probes;

a robotic manipulator, carrying said identification and treatment probes, and operable to move said identification and treatment probes to sight a con-focal region, wherein said identification and treatment probes are supported by a jig assembly that comprises a support member for supporting said identification probe and defining an axis, a plurality of collars coaxially mounted about said axis on said support member with each of said plurality of collars rotatable about said axis, and at least one arced arm attached to each of said plurality of collars, each said at least one arced arm supporting at least one of said plurality of ultrasonic treatment probes, wherein said plurality of ultrasonic treatment probes are received by said at least one arced arm to be focused onto said con-focal region, said con-focal region remaining intersected by said axis as said plurality of collars is rotated about said axis; and a programmed controller for activating said identification and treatment probes and causing motion of said robotic manipulator in a manner such that said ultrasonic identification probe is scanned over at least a portion of the subject tissue to determine a site of a target tumour, and said treatment probes are sighted such that said con-focal region coincides with at least a portion of the target tumour and are activated to ablate the portion of the target tumour.

* * * * *